US010576008B2

(12) United States Patent
Zoss et al.

(10) Patent No.: US 10,576,008 B2
(45) Date of Patent: Mar. 3, 2020

(54) METHODS OF ENHANCING THE REHABILITATION OR TRAINING OF AN EXOSKELETON WEARER

(71) Applicant: Ekso Bionics, Inc., Richmond, CA (US)

(72) Inventors: Adam Zoss, Berkeley, CA (US); Darrell Musick, Los Altos, CA (US); Nathan Harding, Oakland, CA (US)

(73) Assignee: Ekso Bionics, Inc., Richmond, CA (US)

( * ) Notice: Subject to any disclaimer, the term of this patent is extended or adjusted under 35 U.S.C. 154(b) by 247 days.

(21) Appl. No.: 15/524,702

(22) PCT Filed: Nov. 11, 2015

(86) PCT No.: PCT/US2015/060124
§ 371 (c)(1),
(2) Date: May 5, 2017

(87) PCT Pub. No.: WO2016/077442
PCT Pub. Date: May 19, 2016

(65) Prior Publication Data
US 2018/0078442 A1 Mar. 22, 2018

Related U.S. Application Data

(60) Provisional application No. 62/078,114, filed on Nov. 11, 2014.

(51) Int. Cl.
A61H 3/00 (2006.01)
A61H 1/02 (2006.01)
(Continued)

(52) U.S. Cl.
CPC ............... *A61H 3/00* (2013.01); *A61F 2/68* (2013.01); *A61H 1/0255* (2013.01);
(Continued)

(58) Field of Classification Search
CPC .. A61H 1/0214; A61H 1/0237; A61H 1/0255; A61H 1/0262; A61H 2201/5071;
(Continued)

(56) References Cited

U.S. PATENT DOCUMENTS 4,175,550 A 11/1979 Leininger et al.
5,588,841 A 12/1996 Mechling
(Continued)

FOREIGN PATENT DOCUMENTS

| CN | 102058464 | 5/2011 |
| WO | 2014/113456 | 7/2014 |
| WO | 2014/159577 | 10/2014 |

*Primary Examiner* — Dinah Baria
(74) *Attorney, Agent, or Firm* — Diederiks & Whitelaw, PLC.

(57) ABSTRACT

Use of an exoskeleton by a wearer of the exoskeleton is improved through several features. In a first feature, the exoskeleton enters a gait therapy preparation mode to prepare the wearer for subsequent gait therapy. In a second feature, the exoskeleton enters a balance training mode to help the wearer learn to balance while wearing the exoskeleton. In a third feature, the exoskeleton prompts the wearer to shift weight and/or automatically shifts the wearer's weight in a center of pressure control mode. In a fourth feature, an element of variability is introduced into trajectory cycles performed by the exoskeleton in a trajectory cycle mode. Overall, the various disclosed operating modes can be used individually or in various combinations to enhance the rehabilitation or training of the wearer.

20 Claims, 9 Drawing Sheets

(51) Int. Cl.
   *A61F 2/68* (2006.01)
   *A61H 3/02* (2006.01)
(52) U.S. Cl.
   CPC ........... *A61H 1/0262* (2013.01); *A61H 3/008*
   (2013.01); *A61H 3/02* (2013.01); *A61H*
   *2201/165* (2013.01); *A61H 2201/1621*
   (2013.01); *A61H 2201/1642* (2013.01); *A61H*
   *2201/1652* (2013.01); *A61H 2201/501*
   (2013.01); *A61H 2201/5069* (2013.01); *A61H*
   *2201/5071* (2013.01); *A61H 2201/5084*
   (2013.01)
(58) Field of Classification Search
   CPC ...... A61H 2201/5084; A61H 2003/007; A61H
   3/00
   See application file for complete search history.
(56) References Cited

U.S. PATENT DOCUMENTS 5,682,327 A    10/1997  Telepko
   5,901,581 A    5/1999   Chen et al.
   6,872,187 B1   3/2005   Stark et al.
   7,235,039 B2   6/2007   Anders
   7,632,240 B2   12/2009  Schmidtbleicher et al.
   7,803,125 B2   9/2010   Santos-Munne et al.
   7,918,808 B2   4/2011   Simmons
   8,065,105 B2   11/2011  Bar-Haim et al.
   8,323,156 B2   12/2012  Ozawa et al.
   8,556,836 B2   10/2013  Menga
   8,753,296 B2   6/2014   Einav et al.
   8,915,871 B2   12/2014  Einav
   9,610,208 B2   4/2017   Kazerooni et al.
   2008/0132383 A1*  6/2008  Einav ..................... A61H 1/02
                                                        482/8
   2011/0152731 A1   6/2011  Ochi et al.
   2012/0101415 A1   4/2012  Goffer et al.
   2012/0165158 A1   6/2012  Ren et al.
   2013/0226048 A1*  8/2013  Unluhisarcikli ......... A61H 3/00
                                                        601/34
   2014/0142475 A1*  5/2014  Goldfarb ................. A61H 3/00
                                                        601/35
   2014/0171835 A1   6/2014  Solomon et al.

* cited by examiner

METHODS OF ENHANCING THE REHABILITATION OR TRAINING OF AN EXOSKELETON WEARER

CROSS REFERENCE TO RELATED APPLICATIONS

This application claims the benefit of U.S. Provisional Patent Application Ser. No. 62/078,114, which was filed on Nov. 11, 2014 and titled "Methods and Devices for Improving the Rehabilitative Applications of an Ambulatory Exoskeleton". The entire content of this application is incorporated by reference.

FIELD OF THE INVENTION

The present invention relates to devices and methods that aid in the rehabilitation and restoration of muscular function in patients with impaired muscular function or control. More particularly, the present invention relates to device and methods suitable for therapeutic use with patients that have impaired neuromuscular/muscular function of the appendages. Such devices comprise a motorized system of braces and related control systems that potentiate improved function of the appendages for activities including, but not limited to, walking. The invention also relates to utilizing an exoskeleton for training purposes.

BACKGROUND OF THE INVENTION

Millions of individuals suffer from either partial or total loss of walking ability, resulting in greatly impaired mobility for the afflicted individual. This disabled state can occur as the result of traumatic injury, stroke or other medical conditions that cause disorders that affect muscular control. Regardless of origin, the onset and continuance of walking impairment can cause additional negative physical and/or psychological outcomes for the stricken individual. In order to improve the health and quality of life of patients with walking impairment, the development of devices and methods that can improve or restore walking function is of significant utility to the medical and therapeutic communities. Beyond walking impairment, there are a range of medical conditions that interfere with muscular control of the appendages, resulting in loss of function and other adverse conditions for the affected individual. The development of devices and methods to improve or restore these additional functions is also of great interest to the medical and therapeutic communities.

Human exoskeleton devices are being developed in the medical field to restore and rehabilitate proper muscle function for people with disorders that affect muscle control. These exoskeleton devices include a system of motorized braces that can apply forces to the wearer's appendages. In a rehabilitation setting, exoskeletons are controlled by a physical therapist who uses one of a plurality of possible input means to command an exoskeleton control system. In turn, the exoskeleton control system actuates the position of the motorized braces, resulting in the application of force to, and typically movement of, the body of the exoskeleton wearer. Exoskeleton control systems prescribe and control trajectories in the joints of the exoskeleton. These trajectories can be prescribed as position-based, force-based or a combination of both methodologies, such as that seen in an impedance controller. Position-based control systems can modify exoskeleton trajectories directly through modification of the prescribed positions. Force-based control systems can modify exoskeleton trajectories through modification of the prescribed force profiles. Complicated exoskeleton movements, such as walking, are commanded by the exoskeleton control system through the use of a series of exoskeleton trajectories, with increasingly complicated exoskeleton movements requiring an increasingly complicated series of exoskeleton trajectories. These series of trajectories can be cyclic, such as the exoskeleton taking a series of steps with each leg, or they may be discrete, such as an exoskeleton rising from a seated position into a standing position.

Depending on the particular physiology or rehabilitation stage of a patient, it is often beneficial for a physical therapist to interact with the patient in certain ways prior to the use of the exoskeleton in gait training or other types of rehabilitation. In some cases, patients benefit from a stretching, shaking or other manipulation of the limbs in order to prepare the patient for, and thereby increase the rehabilitative benefit of, exoskeleton therapy. Stretching or other loosening up of the limbs can be particularly important for patients who are unable to control certain muscles. In some cases, the physical therapist will work with patients on improving their balance prior to exoskeleton therapy. Improving patient balance while the patient is standing on one or both legs is of clear benefit to subsequent balance during walking by the patient. There exists an unmet need for ways to utilize an exoskeleton to augment or replace the role of a physical therapist in these pre-gait-training (or "pre-gait") functions.

In addition, standing for long periods of times can have detrimental effects on the human body, particularly the feet and legs. As a means to ameliorate some of these effects, such as decreased circulation in the feet, a person, when standing for long periods of time, will consciously or subconsciously shift weight from one foot to another. In some cases, a disabled patient using an exoskeleton device may not be able to feel or be aware of certain issues in the legs and feet, and so this patient would be unlikely to shift weight from foot to foot, which is undesirable should the patient remain standing in the exoskeleton for long periods of time in a fixed position. There exists an unmet need for devices and methods that allow exoskeletons to automatically or manually shift the weight of a patient wearing an exoskeleton device in order to prevent injury or discomfort to the patient, thus aiding in the rehabilitation process.

Furthermore, during a gait training session or in certain other types of physical therapy, exact repetitive motions are of lower therapeutic benefit to a patient than varied motions. Robotics-assisted physical therapy, including exoskeleton therapy, is inherently, due to the nature of robotics, predisposed to execution of exact cycles of repetitive motion, and there exists an unmet need to introduce some degree of variability or randomness into the motions executed by exoskeletons in order to increase the therapeutic benefits of these devices.

SUMMARY OF THE INVENTION

It is an object of the present invention to provide devices and methods that allow a physical therapist or other exoskeleton operator to make use of an exoskeleton for the purpose of preparing the body of a patient for exoskeleton therapy, specifically by causing the exoskeleton to physically manipulate and/or relax the muscles, joints and other parts of the patient in such a way as to prepare the patient to receive exoskeleton therapy, thereby improving the therapeutic benefit of exoskeleton therapy for that patient. It is an additional object of the present invention that this physical preparation of the patient allows for the exoskeleton control system to better predict trajectories during walking and other motions involving both the patient and exoskeleton.

It is also an object of the present invention to provide devices and methods that allow a physical therapist or other exoskeleton operator to make use of an exoskeleton for the purpose of training a patient for exoskeleton therapy, specifically by improving the ability of the patient to balance themselves while coupled to the exoskeleton, thereby improving the therapeutic benefit of exoskeleton therapy for that patient. For patients without sensation of pressure in their feet, as is the case in certain types of injury, this balance information should be presented by other means, and it is an additional object of the present invention to train such a patient to receive center of pressure information from an exoskeleton prior to ambulatory therapy.

It is a further object of the present invention to provide devices and methods that allow for an exoskeleton worn by a patient to change the relative distribution of weight of the patient from one leg to the other, either at set time intervals or in response to certain types of measured data, to prevent injury or discomfort to the patient.

It is another object of the present invention to provide devices and methods that allow for exoskeleton trajectories used in cyclic movements, such as walking, to be altered such that the movements of a patient and exoskeleton have an aspect of irregularity that is of improved therapeutic benefit to the patient. It is an additional object of the present invention that the above-described devices and methods satisfy governmental regulatory (e.g., FDA) requirements with respect to the safety of such exoskeleton usages in a rehabilitation setting.

To achieve these objects, concepts were developed in which a physical therapist, or other exoskeleton operator, is able to use an exoskeleton control system, along with exoskeleton actuators and sensors, for purposes of physically preparing the extremities or other body parts of a patient for a session of gait training or other exoskeleton therapy. Commands from the physical therapist are interpreted by the exoskeleton control system, and the exoskeleton control system engages the actuators of the exoskeleton to move the structure of the exoskeleton. Since the structure of the exoskeleton is coupled to the extremities of the patient, the structure of the exoskeleton applies force to and/or moves the extremities of the patient. The exoskeleton sensors and exoskeleton control system measure information on the state of the exoskeleton and patient, and the exoskeleton control system provides feedback on the state of the exoskeleton and patient to the physical therapist.

Concepts were further developed in which a physical therapist, or other exoskeleton operator, is able to use an exoskeleton control system, along with exoskeleton actuators and sensors, for purposes of preparing a patient for a session of gait training exoskeleton therapy with a pre-gait session of balance training or related skill building. Commands from the physical therapist are interpreted by the exoskeleton control system, and the exoskeleton control system engages the actuators of the exoskeleton to move the structure of the exoskeleton. Since the structure of the exoskeleton is coupled to the extremities of the patient, the structure of the exoskeleton applies force to and/or moves the extremities of the patient. The exoskeleton sensors and exoskeleton control system measure information on the state of the exoskeleton and patient, and the exoskeleton control system provides feedback on the state of the exoskeleton and patient to the physical therapist. Information on the center of pressure is provided to the patient so that the patient can feel when he is balanced over his feet.

Concepts were further developed in which an exoskeleton control system is able to use sensors or other data collection means in order to detect that an exoskeleton wearer has maintained an unfavorable weight distribution for a longer period of time than is desirable. The exoskeleton control system then either prompts the exoskeleton wearer to redistribute his weight or engages exoskeleton actuators in such a way as to affect weight redistribution, with the actuators of the exoskeleton moving the structure of the exoskeleton. Since the structure of the exoskeleton is coupled to the extremities of the exoskeleton wearer, the structure of the exoskeleton applies force to and/or moves the extremities of the patient. The exoskeleton sensors and exoskeleton control system measure information of the state of the exoskeleton and wearer, and the exoskeleton control system provides feedback on the state of the exoskeleton and wearer to the wearer or an exoskeleton operator.

Concepts were further developed in which an element of variability is imposed upon an exoskeleton trajectory sequence by a physical therapist or other exoskeleton operator. This is accomplished by causing an exoskeleton control system to insert an element of variability into the trajectory sequence for certain movements and improves the therapeutic benefit of the exoskeleton to a patient.

In particular, the present invention is directed to methods of improving use of an exoskeleton by a wearer of the exoskeleton. The exoskeleton comprises a control system, a leg support coupled to a leg of the wearer, a hip actuator and a knee actuator. In one embodiment, the exoskeleton is caused to enter a gait therapy preparation mode, wherein the exoskeleton operates to prepare the wearer for therapy, such as by moving the leg of the wearer. The movement of the leg of the wearer can be a low speed movement and can include shaking, vibrating or stretching the leg of the wearer. Following the gait therapy preparation mode, gait therapy can be performed with the exoskeleton.

In accordance with another aspect of the invention, the exoskeleton can be caused to enter a balance training mode in which data is collected on a balance state of the exoskeleton and wearer while the wearer performs a movement. Feedback is provided to the wearer based on the data collected on the balance state of the exoskeleton and wearer. The movement performed by the wearer can be one or more of the following: standing on one leg; marching in place; shifting weight from leg to leg; shifting weight between legs and crutches; sidestepping; or backstepping. An amount of assistance need to stabilize the exoskeleton and wearer is calculated and provided. The feedback to the wearer includes information on the amount of assistance needed.

For a further aspect, a center of pressure of the exoskeleton and wearer is calculated, and a determination is made as to whether a weight shift is recommended. If it is determined that a weight shift is recommended, the wearer is prompted to perform the weight shift. If the wearer does not perform the weight shift, at least one trajectory needed to perform the weight shift is calculated. The weight shift is performed by moving the exoskeleton through the at least one trajectory. Alternatively, if it is determined that a weight shift is recommended, the wearer need not be prompted, and the at least one trajectory needed to perform the weight shift is calculated and the weight shift is automatically performed by moving the exoskeleton through the at least one trajectory.

In accordance with a still further aspect, the exoskeleton is directed to perform a trajectory cycle a plurality of times.

The trajectory cycle is modified to create a first modified trajectory cycle, and the exoskeleton is caused to perform the first modified trajectory cycle one or more times. After the exoskeleton has performed the first modified trajectory cycle the one or more times, the trajectory cycle is modified to create a second modified trajectory cycle, and the exoskeleton is caused to perform the second modified trajectory cycle one or more times. By way of example, trajectory cycle can be a step, and modifying the trajectory cycle can include changing one or more of the following parameters: step height; step length; step time; or step spacing. The first modified trajectory cycle is deleted after the exoskeleton has performed the first modified trajectory cycle the one or more times.

Additional objects, features and advantages of the invention will become more readily apparent from the following detailed description of the invention when taken in conjunction with the drawings wherein like reference numerals refer to corresponding parts in the several views.

DETAILED DESCRIPTION OF THE PREFERRED EMBODIMENTS

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

In connection with the present invention, "center of pressure" is the term given to the point of application of the ground reaction force vector. The ground reaction force vector represents the sum of all forces acting between a physical object and its supporting surface, e.g., between an exoskeleton and the ground. The center of pressure is not a static outcome measure. For instance, during walking, the center of pressure is near the heel at the time of heelstrike and moves anteriorly throughout the step, being located near the toes at toe-off.

Figure 1:
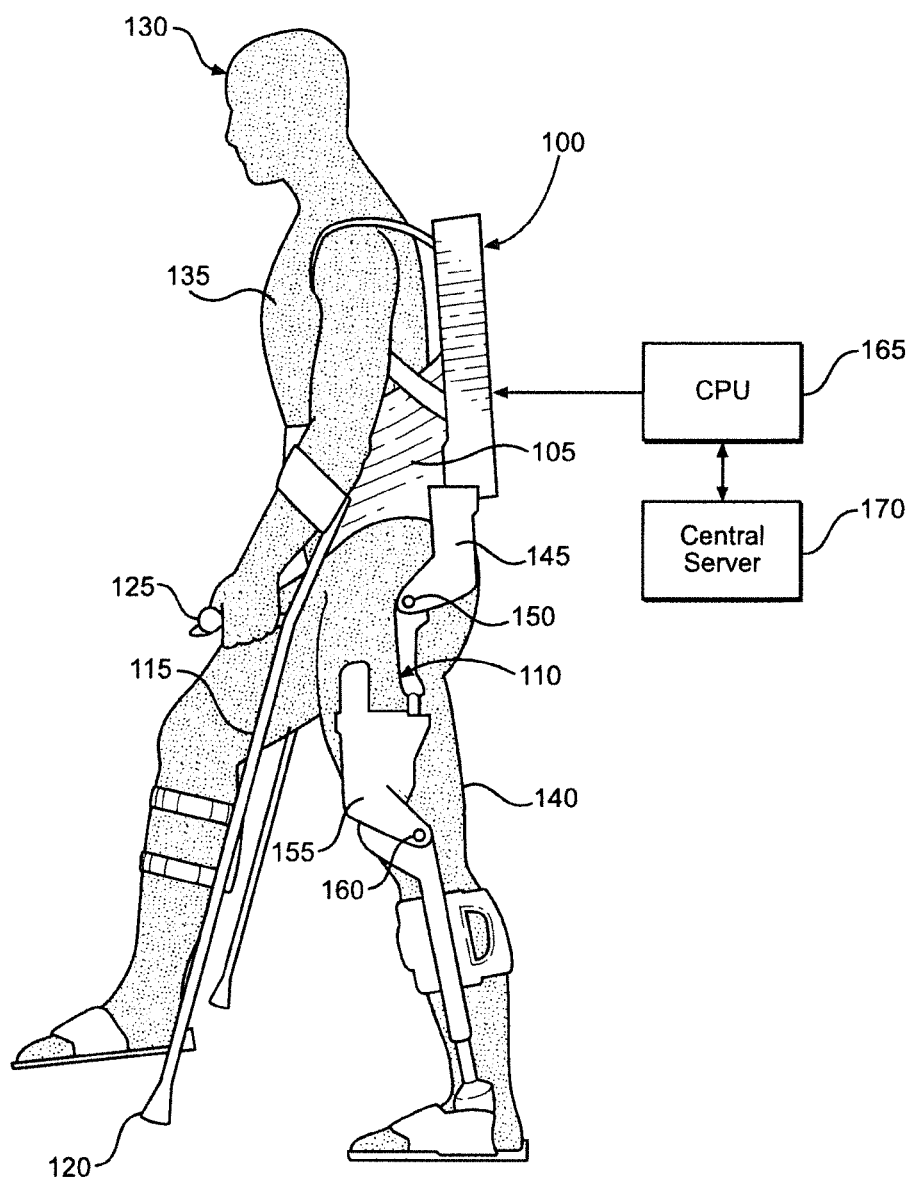
FIG. 1 is a side view of an individual wearing an ambulatory exoskeleton.

With reference to FIG. 1, an exoskeleton (or exoskeleton device) 100 has a torso brace 105 and leg supports (one of which is labeled 110). Exoskeleton 100 is used in combination with a pair of crutches, e.g., a left crutch 115 which includes a lower, ground engaging tip 120 and a handle 125. In connection with this embodiment, through the use of exoskeleton 100, a patient (or, more generally, a user or wearer) 130 is able to walk. In a manner known in the art, torso brace 105 is configured to be coupled to a torso 135 of patient 130, while the leg supports are configured to be coupled to the lower limbs (one of which is labeled 140) of patient 130. Additionally, actuators are interposed between portions of the leg supports 110, as well as between the leg supports 110 and torso brace 105, and provided for shifting of the leg supports 110 relative to torso brace 105 to enable movement of the lower limbs 140 of patient 130. In some embodiments, torso brace 105 can be quite small and comprise a pelvic link (not shown), which wraps around the pelvis of patient 130. In the example shown in FIG. 1, the actuators are specifically shown as a hip actuator 145, which is used to move a hip joint 150 in flexion and extension, and as knee actuator 155, which is used to move a knee joint 160 in flexion and extension. The actuators 145 and 155 can be controlled by a controller (or CPU) 165 in a plurality of ways known to one skilled in the art of exoskeleton control, with controller 165 being a constituent of an exoskeleton control system. Although not shown in FIG. 1, various sensors are in communication with controller 165 so that controller 165 can monitor the orientation of exoskeleton 100. Such sensors can include, without restriction, encoders, potentiometers, accelerometer and gyroscopes, for example. In addition, controller 165 can be in continuous or intermittent communication with, and can report collected data to, a central server 170. As the particular structure of an exoskeleton for use in connection with the present invention can take various forms known in the art, it will not be detailed further herein.

Figure 2A:
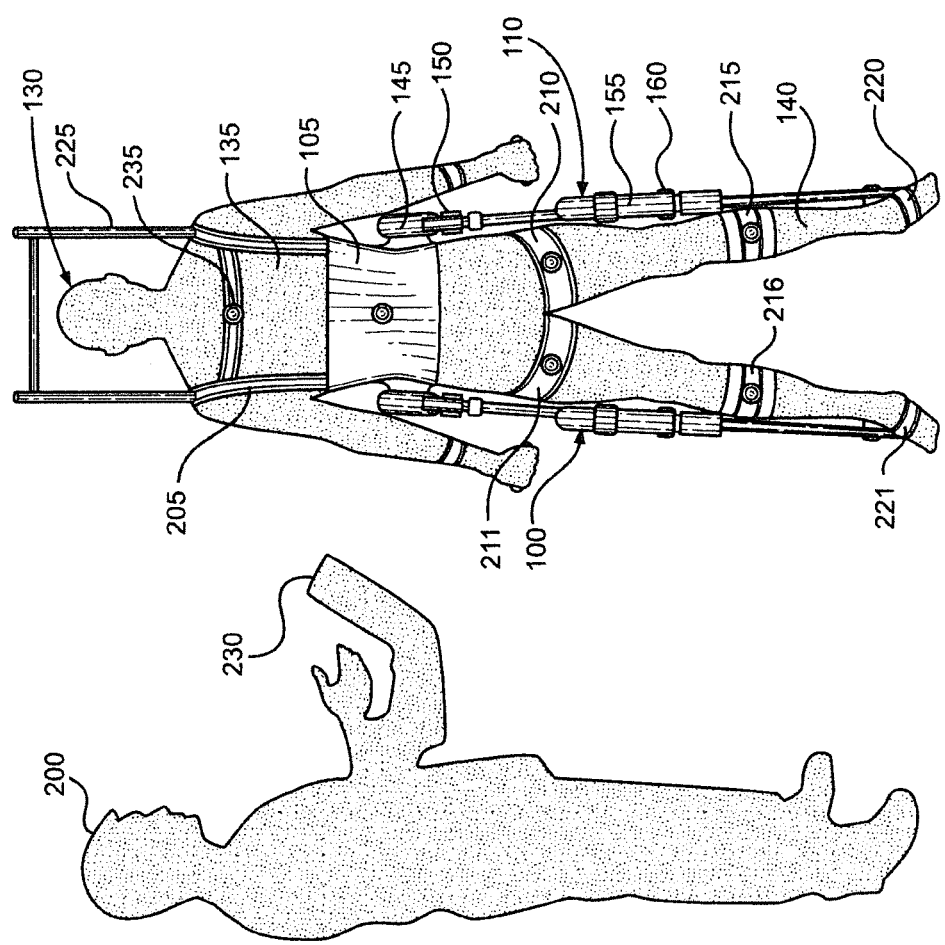
FIG. 2A shows a physical therapist observing and interacting with an individual and exoskeleton in accordance with a first embodiment of the present invention.

Turning to FIG. 2A, there is shown a physical therapist 200 observing patient 130 and exoskeleton 100 having a trunk portion (not separately labeled) in accordance with a first embodiment of the present invention. As shown in this particular exoskeleton arrangement, patient 130 is coupled to exoskeleton 100 by torso brace 105, chest strapping 205, upper leg braces 210 and 211, lower leg braces 215 and 216 and foot braces 220 and 221. In some cases, depending on the rehabilitative state of patient 130, patient 130 and exoskeleton 100 are supported by a harness 225, which is connected to chest strapping 205. Physical therapist 200 uses a control or interface device 230, shown as a laptop in FIG. 2A, to transmit commands to the exoskeleton control system (e.g., controller 165) of exoskeleton 100 to cause exoskeleton 100 to engage in movements, with hip actuator 145 effecting movements about hip joint 150 and knee actuator 155 effecting movements about knee joint 160. When hip actuator 145 causes movement about hip joint 150, force is exerted upon an upper leg of patient 130 through upper leg brace 210, including movement of the upper leg relative to torso 135 of patient 130. Similarly, when knee actuator 155 causes movement about knee joint 160, force is exerted upon a lower leg of patient 130 through lower leg brace 215, including movement of the lower leg relative to the upper leg of patient 130. A plurality of sensors (one of which is labeled 235) is mounted at various positions where exoskeleton 100 interacts with patient 130, with the plurality of sensors transmitting information to physical therapist 200 through control device 230.

Figure 2B:
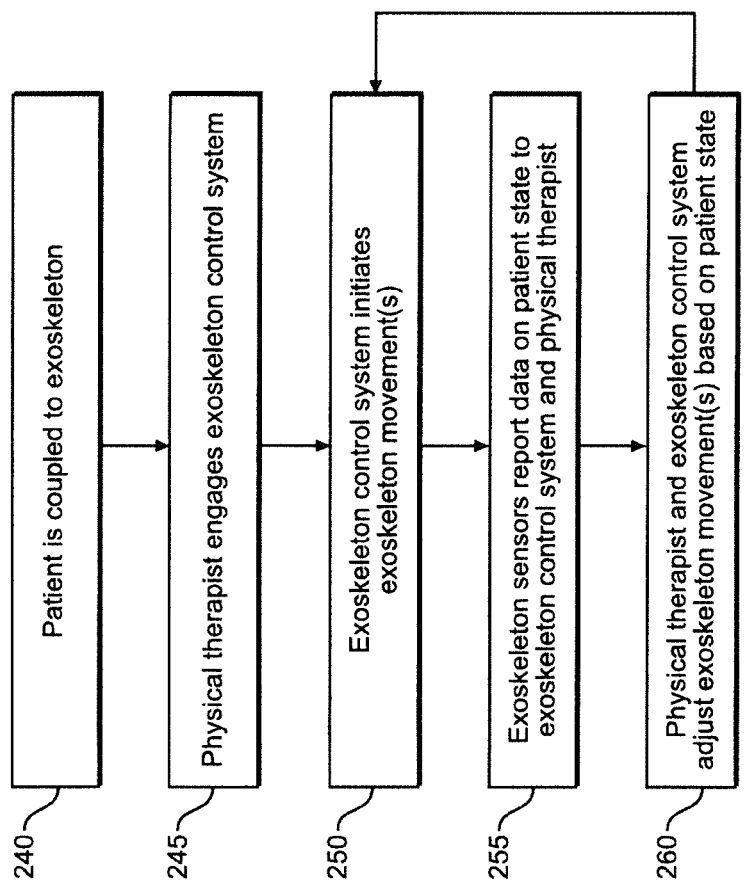
FIG. 2B is a flowchart illustrating the first embodiment in which the physical therapist makes use of the exoskeleton to stretch and/or otherwise prepare the body of the individual for exoskeleton therapy.

FIG. 2B is a flowchart illustrating a method in accordance with the first aspect of the present invention which is directed to operating exoskeleton 100 in an initial gait therapy preparation mode of operation. At step 240, physical therapist 200 couples patient 130 to exoskeleton 100. At step 245, physical therapist 200 engages the exoskeleton control system, i.e., physical therapist 200 causes commands to be transmitted to the control system, these commands directing exoskeleton 100 to enter a gait therapy preparation mode and initiate a movement or sequence of movements. At step 250, the exoskeleton control system causes exoskeleton 100 to perform the commanded movement or sequence of movements, likely a low intensity and low speed movement, which results in force being exerted on and movement of patient 130. At step 255, the plurality of sensors are employed to collect and report data on the state of patient 130 to the exoskeleton control system and physical therapist 200, with this data indicating such things as the amount of force being exerted on patient 130, the amount of resistance the patient's body is exerting on exoskeleton 100, as well as position-based information. At step 260, the exoskeleton control system and physical therapist 200 interpret the data provided by the plurality of sensors regarding the state of exoskeleton 100 and patient 130, with this data then being used to make changes or corrections to future exoskeleton movements or sequences of movements. The above process repeats until physical therapist 200 is satisfied that patient 130 is adequately stretched, relaxed or otherwise physically prepared for a subsequent exoskeleton therapy session at which point physical therapist 200 causes exoskeleton 100 to exit the gait therapy preparation mode. In some embodiments, the motion exerted by exoskeleton 100 on patient 130 is a shaking or vibrational motion upon the muscles and/or joints of patient 130. In other embodiments, the motion exerted by exoskeleton 100 on patient 130 is a stretching of the muscles and/or joints of patient 130. In still other embodiments, the motion exerted by exoskeleton 100 upon patient 130 is another, different type of motion known in the art of physical therapy, i.e., the exoskeleton is used to perform other patient manipulation roles of the physical therapist. In some embodiments, the exoskeleton control system calculates the amount of force exerted upon patient 130, using joint torque, position change and other values, preferably independently of pressure sensors.

As an example of the first aspect, consider a physical therapist working with a paraplegic patient who, due to injury, has not moved his/her legs in a long period of time. The muscles, joints and tendons in the patient's legs are predictably stiff. Through use of the gait therapy preparation mode, the physical therapist is able to loosen up and stretch the legs of the patient prior to a session of exoskeleton therapy, which will improve the rehabilitative benefit of the subsequent exoskeleton therapy session for the patient.

Figure 3A:
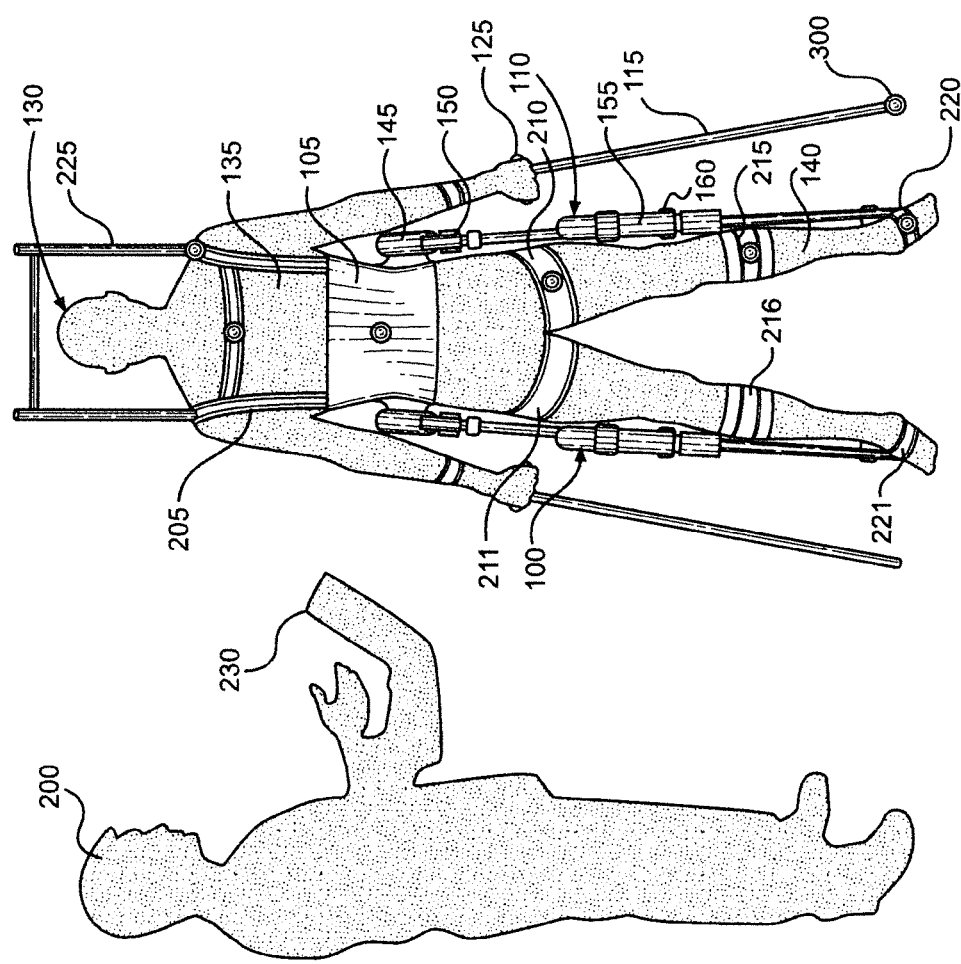
FIG. 3A shows a physical therapist observing and interacting with an individual and exoskeleton in accordance with a second embodiment of the present invention.
Figure 3B:
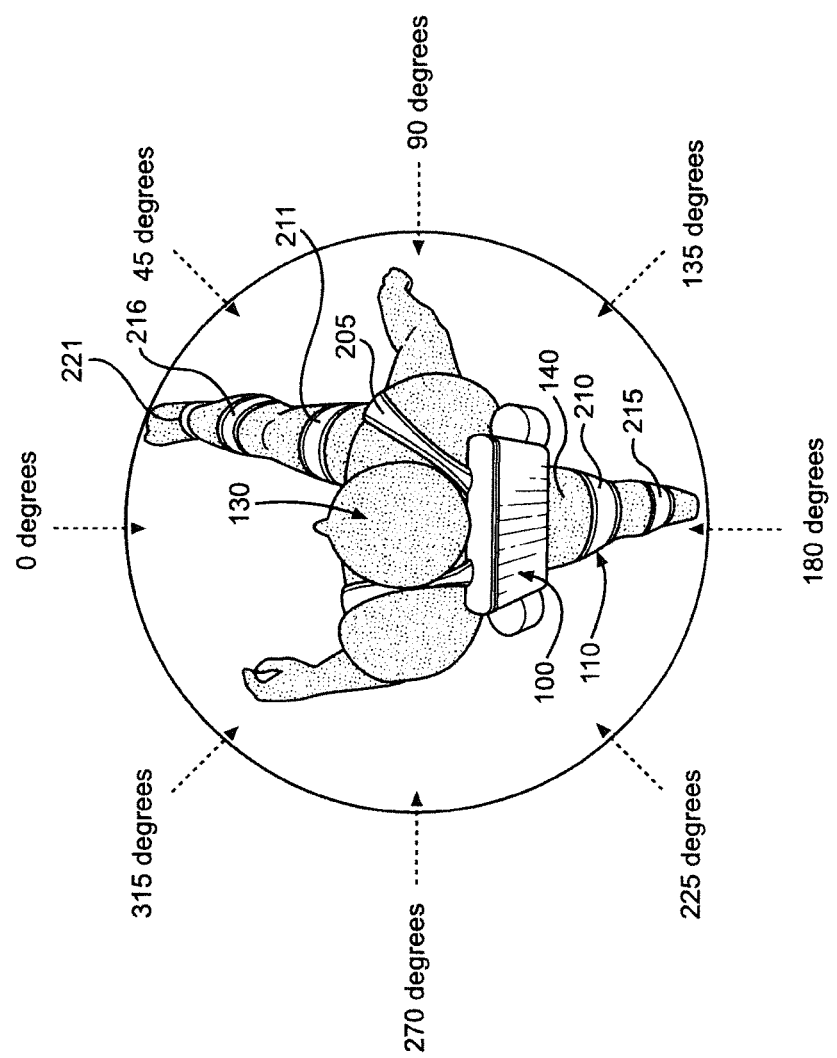
FIG. 3B is a top view of an individual wearing an ambulatory exoskeleton.

With reference now to FIG. 3A, there is shown physical therapist 200 observing patient 130 and exoskeleton 100, particularly in connection with a second aspect of the present invention relating to a balancing training mode or session. As in FIG. 2A, patient 130 is coupled to exoskeleton 100 by torso brace 105, chest strapping 205, upper leg braces 210 and 211, lower leg braces 215 and 216 and foot braces 220 and 221. In some cases, depending on the rehabilitative state of patient 130, patient 130 and exoskeleton 100 are supported by a harness 225, which is connected to chest strapping 205. Physical therapist 200 uses a control device 230, shown as a laptop in FIG. 3A, to transmit commands to the exoskeleton control system of exoskeleton 100 to cause exoskeleton 100 to engage in movements, with hip actuator 145 effecting movements about hip joint 150 and knee actuator 155 effecting movements about knee joint 160. When hip actuator 145 causes movement about hip joint 150, force is exerted upon an upper leg of patient 130 through upper leg brace 210, including movement of the upper leg relative to torso 135 of patient 130. Similarly, when knee actuator 155 causes movement about knee joint 160, force is exerted upon a lower leg of patient 130 through lower leg brace 215, including movement of the lower leg relative to the upper leg of patient 130. In some cases, patient 130 uses the pair of crutches described in connection with FIG. 1 to interact with the ground in order to assist patient 130 with balancing. A plurality of sensors (one of which is labeled 300) is mounted at various positions on exoskeleton 100 and the pair of crutches, and the plurality of sensors transmits information to the exoskeleton control system of exoskeleton 100 and physical therapist 200 through control or interface device 230. FIG. 3B is a top view of patient 130 and exoskeleton 100 and shows the various angles in the transverse plane through which patient 130 and exoskeleton 100 can move or shift weight in the course of a balance training session.

Figure 3C:
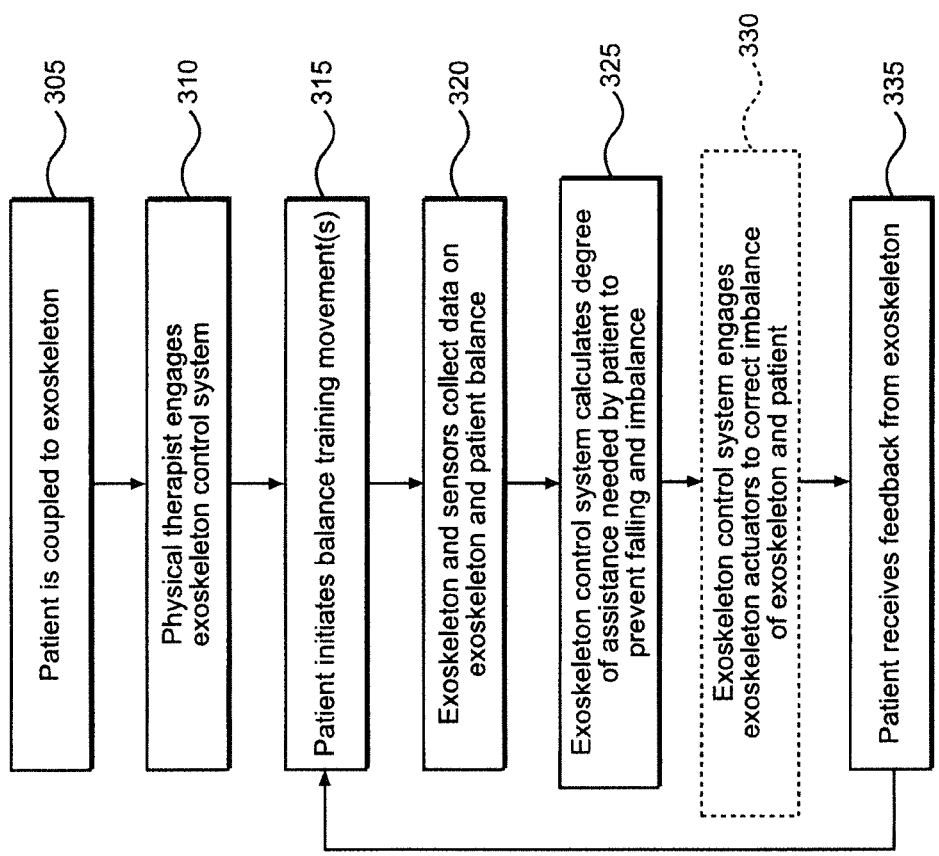
FIG. 3C is a flowchart illustrating the second embodiment in which the physical therapist makes use of the exoskeleton for pre-gait training of the individual.

FIG. 3C is a flowchart illustrating a method in accordance with this aspect of the invention. At step 305, physical therapist 200 couples patient 130 to exoskeleton 100. At step 310, physical therapist 200 engages the exoskeleton control system, i.e., physical therapist 200 causes commands to be transmitted, such as through interface or control device 230, to the control system, with these commands directing exoskeleton 100 to enter a balance training mode. At step 315, patient 130 performs a balance training movement or sequence of movements. At step 320, the exoskeleton control system and the plurality of sensors collect data relating to the balance of exoskeleton 100 and patient 130. At step 325, the exoskeleton control system uses the data from step 320 in an algorithm to calculate the degree of imbalance and risk of falling in order to determine what degree of assistance, if any, should be provided by exoskeleton 100 in order stabilize exoskeleton 100 and patient 130. If, in step 325, the exoskeleton control system determines that stabilization of exoskeleton 100 is required, the exoskeleton control system calculates the required exoskeleton trajectories and engages the exoskeleton actuators in step 330, thereby restoring stability to patient 130 and exoskeleton 100. At step 335, patient 130 receives feedback from exoskeleton 100 as to his performance and balance, including the degree of assistance rendered by exoskeleton 100. The above process repeats until physical therapist 200 or patient 130 determines that balance training is complete. In some embodiments, a center of pressure is used to calculate exoskeleton balance based on information from pressure sensors on the feet of exoskeleton 100 and the pair of crutches. In other embodiments, balance is calculated based on exoskeleton joint angles or exoskeleton trajectories. In still other embodiments, balance is calculated using additional data from accelerometers, tilt sensors or other types of sensors known in the art. Feedback can be provided from exoskeleton 100 to patient 130 based on balance performance in certain balance training tasks and/or feedback on patient balance performance can be provided from exoskeleton 100 to physical therapist 200. Exoskeleton 100 can utilize detailed feedback in order direct patient 130 to balance on a specific point or multiple points in a series. For instance, exoskeleton 100 can utilize the amount of work performed by patient 130 or data collected from pressure sensors between exoskeleton 100 and patient 130 when determining balance point targets. In some embodiments, the exoskeleton control system tunes balance targets based on the performance and rehabilitative state of patient 130 in prior or ongoing balance exercises. In some embodiments, balance training focuses on teaching patients with specific injuries, such as stroke, to trust the patient's weaker leg or side. In some embodiments, the balance training involves patient 130: standing on one leg; marching in place; shifting weight from leg to leg; shifting weight between legs and crutches; and/or sidestepping or backstepping.

By way of example, consider a physical therapist working with a disabled patient who has not yet attempted walking while using an ambulatory exoskeleton. By making use of the balance training mode, the physical therapist is able to teach the patient how to better balance themselves and the exoskeleton in a safe manner prior to attempting more complicated motions such as walking.

With respect to both of modes discussed with reference to FIGS. 2 and 3, the sensors can be pressure sensors or other sensor types known in the art. In some embodiments, the sensors are located in different and/or additional positions than those shown in FIGS. 2A and 3A. In certain embodiments, harness 225 is motorized so as to assist patient 130 in standing or sitting. In any case, patient 130 and/or the exoskeleton control system fill some or all of the roles of physical therapist 200, including autonomous use of exoskeleton 100 by patient 130 for stretching, balance training, etc., with the exoskeleton control system and the plurality of sensors providing safety measures in this process.

Figure 4:
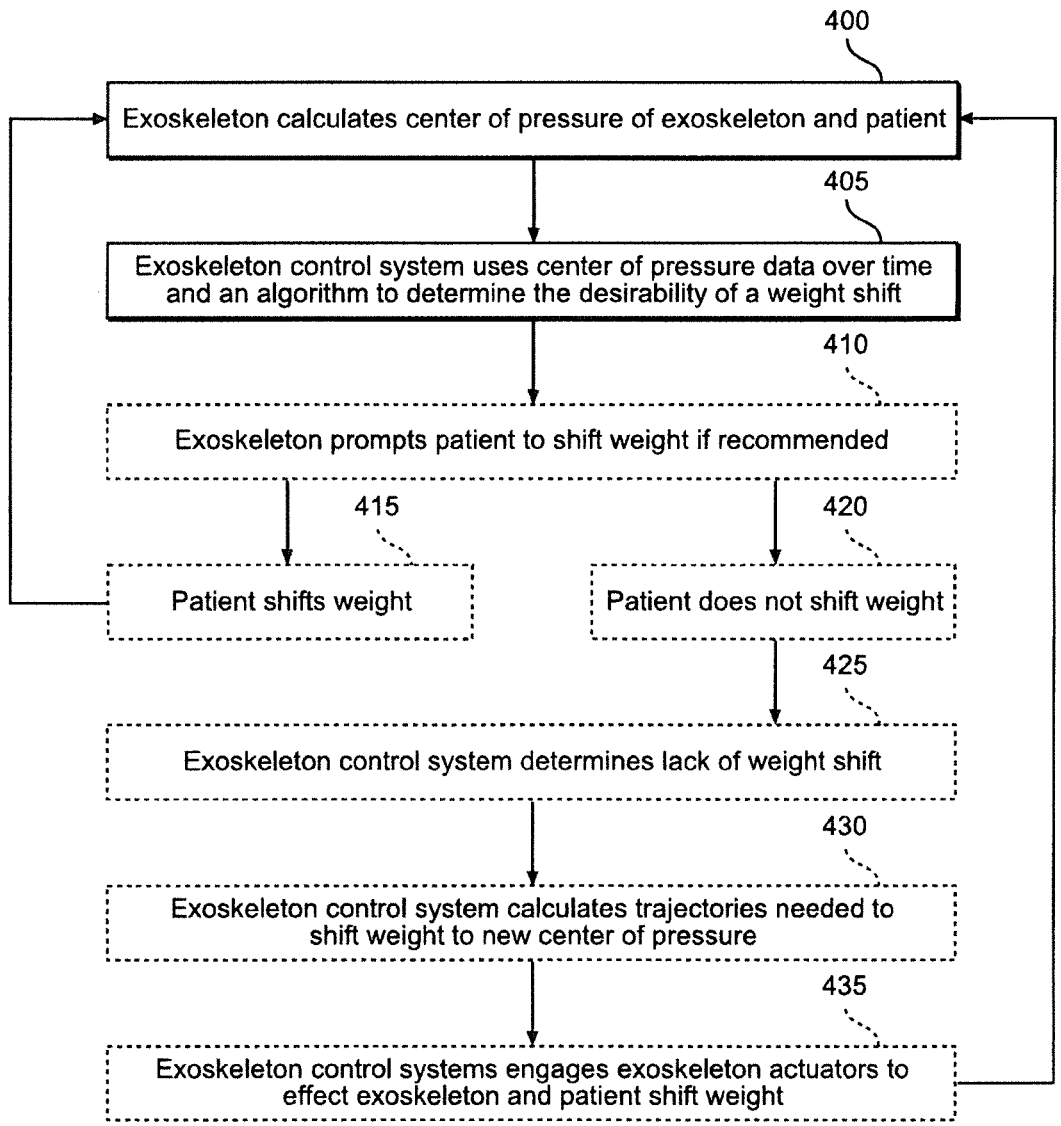
FIG. 4 is a flowchart illustrating a third embodiment of the present invention.

With reference now to FIG. 4, a flowchart illustrates a method in accordance with a third aspect of the invention in connection with a center of pressure control mode. At step 400, the exoskeleton control system uses the plurality of sensors or exoskeleton state or pose data to calculate the center of pressure of exoskeleton 100 and patient 130. At step 405, the exoskeleton control system uses the center of pressure data from step 400, measured over time, and an algorithm to determine if the center of pressure of exoskeleton 100 and patient 130 should be shifted. At step 410, exoskeleton 100 prompts patient 130 to shift weight if a weight shift is recommended. At step 415, patient 130 shifts weight manually in response to the prompt in step 410, and the system cycles back to step 400 when this weight shift is detected. Alternatively, at step 420, patient 130 does not shift weight in response to the prompt in step 410. As a result, at step 425, the exoskeleton control system determines that patient 130 has not shifted weight after a given period of time following the prompt in step 410. At step 430, the exoskeleton control system calculates the exoskeleton trajectories needed to shift the exoskeleton weight to a new center of pressure. At step 435, the exoskeleton control system engages the exoskeleton actuators to effect exoskeleton and patient weight shift, and the system then cycles back to step 400. In some embodiments, such as a "manual" mode, steps 425, 430 and 435 are omitted, and exoskeleton 100 just provides feedback to patient 130 on the desirability of a weight shift. In other embodiments, such as an "automatic" mode, patient 130 is not prompted to shift weight, and steps 410, 415, 420 and 425 are omitted, with exoskeleton 100 automatically shifting weight when the exoskeleton control system determines the desirability of doing so. Knowledge of the center of pressure is used by a person to feel when he/she is balanced over his/her feet. For users without sensation of pressure in their feet, however, this information, including current and desired centers of pressure, is presented in other ways. In some embodiments, feedback takes the form of sound, vibration, visual feedback or other types of feedback known in the art. Additional sensors can be used to measure the state of patient 130 and are factored into the determination of the desirability of a weight shift along with center of pressure data over time. In some embodiments, data from additional devices is considered by the exoskeleton control system, such as pressure sensors attached to the pair of crutches or the arms of patient 130, with this data being factored into the determination of the desirability of a weight shift. In addition, the center of mass of the exoskeleton system can be considered by the exoskeleton control system.

As an example of the third embodiment, consider a disabled person who is using an ambulatory exoskeleton outside of a physical therapy setting, such as in the home. If this person, who has no sensation below the waist, is using the exoskeleton to enable himself/herself to stand for long periods of time, such as when he/she is engaged in cooking activities, the exoskeleton will periodically determine that the person should shift weight and prompt him/her to do so. The person, who would otherwise be unable to sense that he/she had been standing with too much weight on a single leg for too long, then shifts weight in response to the prompt from the exoskeleton, with this prompt taking the form of an audio cue or a vibration in an area where the person still has sensation. If the person does not respond to the prompt by shifting weight, then, after a certain period, the exoskeleton shifts the weight of the person automatically. In this way, injuries to or discomfort in the lower extremities of the person due to extended standing in a single position can be prevented.

Figure 5A:
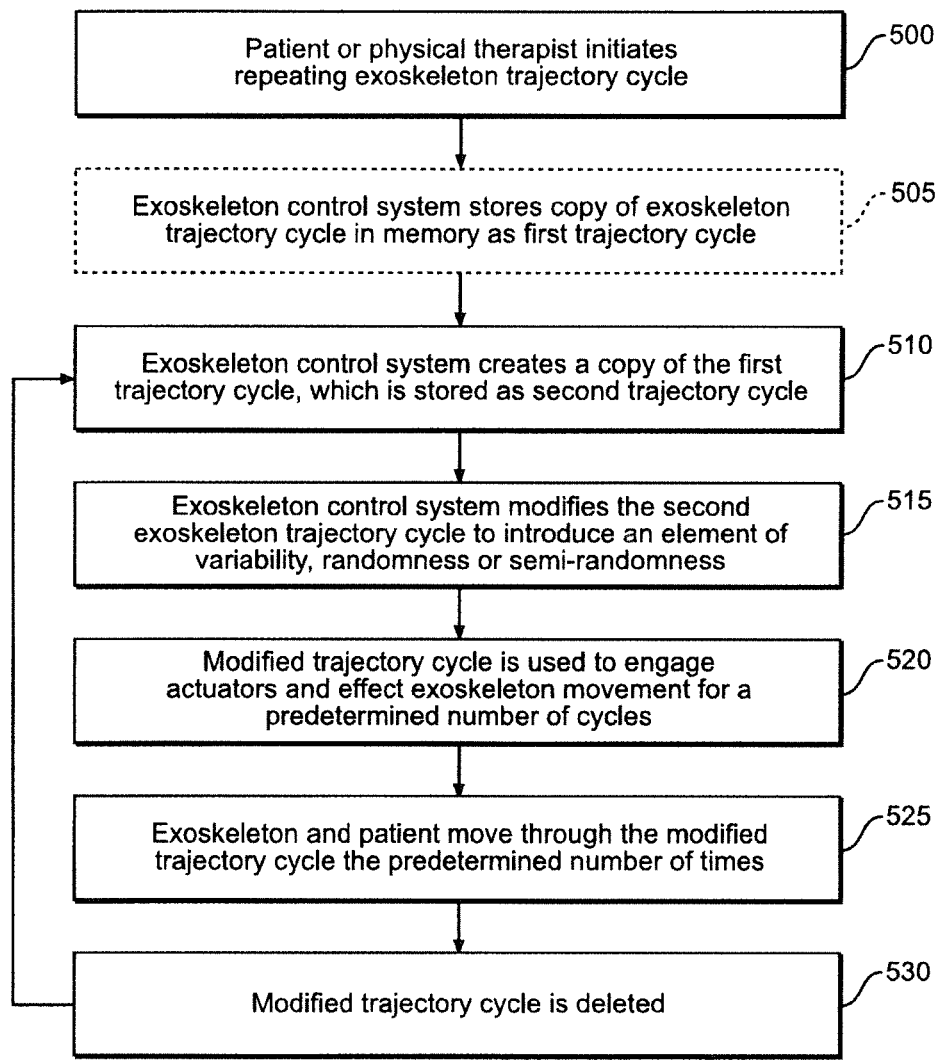
FIG. 5A is a flowchart illustrating a fourth embodiment of the present invention.

Turning to FIG. 5A, a flowchart illustrates a method in accordance with a fourth, trajectory cycle mode aspect of the present invention. At step 500, patient 130 or physical therapist 200 initiates a repeating exoskeleton trajectory cycle. At step 505, the exoskeleton control system stores a copy of the exoskeleton trajectory cycle in memory as a first trajectory cycle. Alternatively, if the exoskeleton trajectory cycle was already stored in memory as the first trajectory cycle, step 505 can be omitted. At step 510, the exoskeleton control system creates a copy of the first trajectory cycle, which is stored in memory as a second trajectory cycle. At step 515, the exoskeleton control system modifies the second trajectory cycle to introduce an element of variability, randomness or semi-randomness to the parameters of the trajectory cycle. At step 520, the exoskeleton control system uses the modified trajectory cycle from step 515 to engage exoskeleton actuators and effect exoskeleton movement for a predetermined number of trajectory cycles (e.g., 1-3). As a result, at step 525, exoskeleton 100 and patient 130 move thorough the modified trajectory cycle the predetermined number of times. At step 530, the modified trajectory cycle from step 515 is deleted, and the control system cycles to step 510, in which the exoskeleton control system creates a new copy of the first trajectory cycle, with the process repeating in each additional trajectory cycle or set of trajectory cycles undertaken by exoskeleton 100. This increase in variability for cyclic movements improves the rehabilitative benefit to patients. In some embodiments, one or more of the following parameters are altered during modification of a trajectory cycle: step height; step length; step time; and step spacing. In other embodiments, parameters unrelated to step are altered. In certain embodiments, is limited to within certain selectable parameters and/or is restricted by patient safety parameters.

As an example of the fourth embodiment, consider a physical therapist working with a disabled patient in order to improve the walking ability of that patient. By use of the trajectory cycle mode of the present invention, step parameters are automatically altered by the exoskeleton, resulting in greater rehabilitative benefit to the patient and faster improvement in the patient's gait.

Figure 5B:
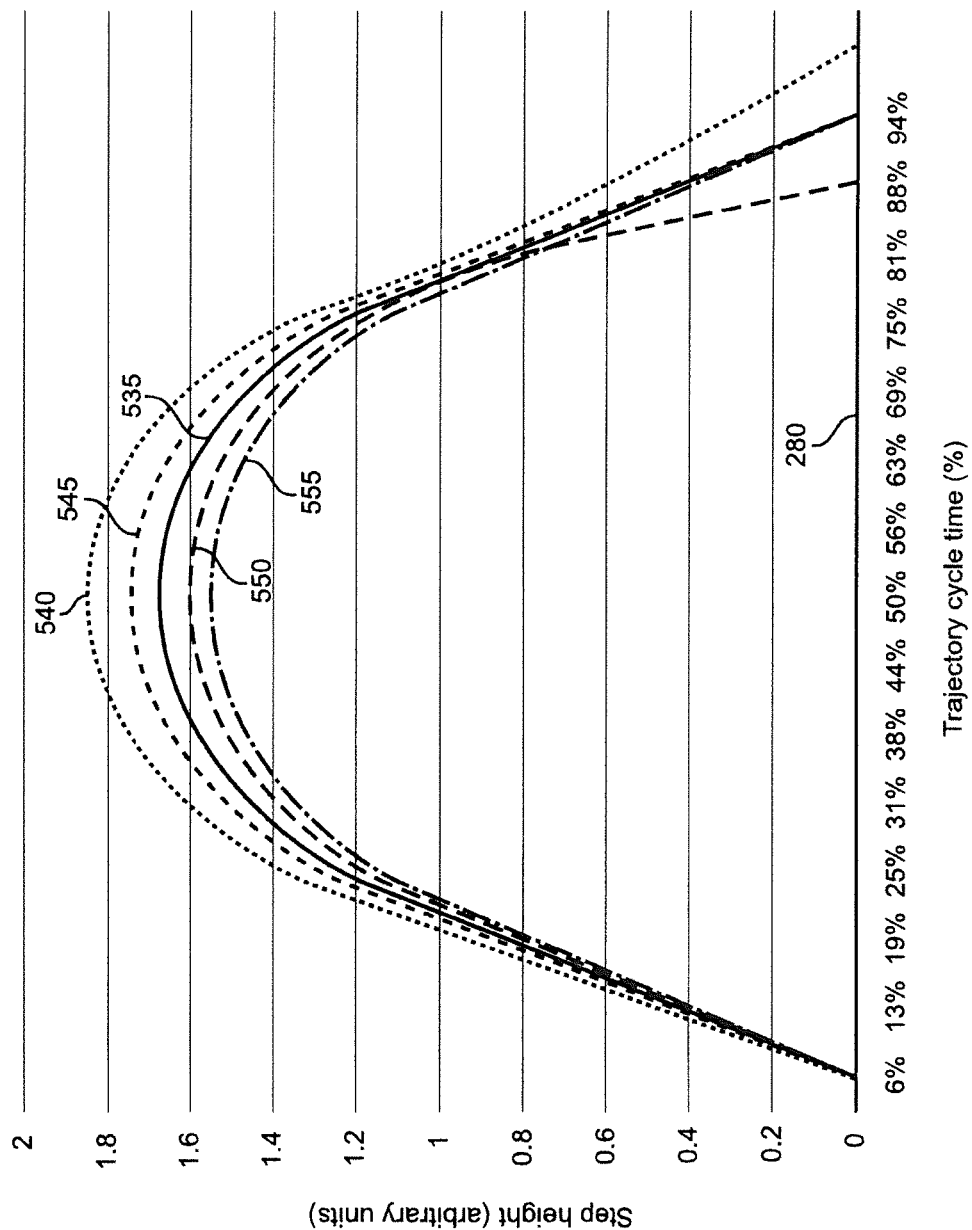
FIG. 5B is a graph of example modified trajectories in accordance with the fourth embodiment.

With reference to FIG. 5B, there is shown a graph of exemplary modified trajectory cycles used in exoskeleton walking in accordance with this aspect of the invention. Step height is plotted on the Y-axis versus the percentage of the trajectory cycle time on the X-axis, with one trajectory cycle (0-100%) representing a single step. A line 535 represents the step height over time of an unmodified trajectory cycle, while lines 540, 545, 550 and 555 represent modified trajectory cycles. In this example, by varying the step height of the trajectory cycle as described above in connection with FIG. 5A, each of the steps resulting from these trajectory cycles would have slightly different exoskeleton and patient step heights. Also, relative to the unmodified trajectory cycle represented by line 535, the modified trajectory cycle represented by line 540 has a longer step time, and the modified trajectory cycle represented by line 550 has a shorter step time.

Based on the above, it should be readily apparent that the present invention provides an exoskeleton with improved rehabilitative benefit through the exoskeleton's ability to perform stretching, balance training, weight shifting and variable trajectory cycles. In connection with the invention, the exoskeleton user or wearer can be a disabled person receiving treatment from a physical therapist, a disabled person operating the exoskeleton in the absence of a physical therapist or even an abled-bodied person, such as an able-bodied person working with a trainer. In any case, the various disclosed operating modes can be used individually or in various combinations successively to enhance the rehabilitation or training of the user. Although described with reference to preferred embodiments, it should be readily understood that various changes or modifications could be made to the invention without departing from the spirit thereof. In general, the invention is only intended to be limited by the scope of the following claims.

The invention claimed is:

1. A method of using an exoskeleton, including a control system, a leg support coupled to a leg of a wearer, a hip actuator and a knee actuator, the method comprising:
   causing the exoskeleton to enter a gait therapy preparation mode;
   moving the leg of the wearer with the exoskeleton during the gait therapy preparation mode;
   causing the exoskeleton to exit the gait therapy preparation mode; and
   after exiting the gait therapy preparation mode, performing gait therapy with the exoskeleton during which the wearer walks.

2. The method of claim 1, wherein moving the leg of the wearer includes performing a low speed movement of the leg of the wearer with the exoskeleton.

3. The method of claim 1, wherein moving the leg of the wearer includes shaking, vibrating or stretching the leg of the wearer with the exoskeleton.

4. A method of using an exoskeleton, including a control system, a leg support coupled to a leg of a wearer, a hip actuator and a knee actuator, in a balance training mode, the method comprising:
   causing the exoskeleton to enter the balance training mode;
   collecting data on a balance state of the exoskeleton and wearer while the wearer performs a movement; and
   providing feedback to the wearer based on the data collected on the balance state of the exoskeleton and wearer.

5. The method of claim 4, wherein collecting data includes collecting data on the balance state of the exoskeleton and wearer while the wearer performs one or more of the following movements: standing on one leg; marching in place; shifting weight from leg to leg; shifting weight between legs and crutches; sidestepping; or backstepping.

6. The method of claim 5, further comprising:
   calculating an amount of assistance needed to stabilize the exoskeleton and wearer; and
   providing the amount of assistance needed to stabilize the exoskeleton and wearer, wherein providing feedback to the wearer includes providing information on the amount of assistance needed to stabilize the exoskeleton and wearer.

7. A method of using an exoskeleton, including a control system, a leg support coupled to a leg of a wearer, a hip actuator and a knee actuator, in a center of pressure control mode, the method comprising:
   causing the exoskeleton to enter the center of pressure control mode;
   calculating a center of pressure of the exoskeleton and wearer; and
   determining whether a weight shift is recommended based on an elapsed time while the wearer is standing in place.

8. The method of claim 7, further comprising:
   prompting the wearer to perform the weight shift if it is determined that a weight shift is recommended.

9. The method of claim 8, further comprising:
   determining that the wearer has not performed the weight shift;
   calculating at least one trajectory needed to perform the weight shift; and
   automatically performing the weight shift by moving the exoskeleton through the at least one trajectory.

10. The method of claim 7, further comprising:
    calculating at least one trajectory needed to perform the weight shift if it is determined that a weight shift is recommended; and
    automatically performing the weight shift by moving the exoskeleton through the at least one trajectory.

11. A method of using an exoskeleton, including a control system, a leg support coupled to a leg of a wearer, a hip actuator and a knee actuator, in a trajectory cycle mode, the method comprising:
    causing the exoskeleton to enter the trajectory cycle mode;
    directing the exoskeleton to perform a trajectory cycle a plurality of times;
    modifying the trajectory cycle to create a first modified trajectory cycle by introducing an element of variability, randomness or semi-randomness to the trajectory cycle; and
    causing the exoskeleton to perform the first modified trajectory cycle one or more times.

12. The method of claim 11, further comprising:
    modifying the trajectory cycle to create a second modified trajectory cycle; and
    causing the exoskeleton to perform the second modified trajectory cycle one or more times after the exoskeleton has performed the first modified trajectory cycle the one or more times.

13. The method of claim 11, wherein directing the exoskeleton to perform the trajectory cycle the plurality of times includes directing the exoskeleton to perform a step the plurality of times.

14. The method of claim 13, wherein modifying the trajectory cycle includes changing one or more of the following parameters: step height; step length; step time; or step spacing.

15. The method of claim 11, further comprising:
deleting the first modified trajectory cycle after the exoskeleton has performed the first modified trajectory cycle the one or more times.

16. The method of claim 11, wherein each of the trajectory cycle and the first modified trajectory cycle comprises a full step.

17. A method of using an exoskeleton including a control system, a leg support coupled to a leg of a wearer, a hip actuator and a knee actuator, the method comprising:
causing the exoskeleton to successively enter at least two modes of operation for the exoskeleton, with the modes of operation being selected from two or more of a gait therapy preparation mode, a balance training mode, a center of pressure control mode, and a trajectory cycle mode, wherein:
a) in the gait therapy preparation mode, a low speed movement of the leg of the wearer with the exoskeleton is performed prior to performing gait therapy on the wearer utilizing the exoskeleton;
b) in the balance training mode, data is collected on a balance state of the exoskeleton and wearer while the wearer performs a movement and feedback is provided to the wearer based on the data collected on the balance state of the exoskeleton and wearer;
c) in the pressure control mode, a center of pressure of the exoskeleton and wearer is calculated and a determination is made a weight shift is recommended; and
d) in the trajectory cycle mode, the exoskeleton is caused to perform a trajectory cycle a plurality of times, a first modified trajectory cycle is created, and the exoskeleton is caused to perform the first modified trajectory cycle one or more times.

18. The method of claim 17, wherein, in the gait therapy preparation mode, the low speed movement includes shaking, vibrating or stretching the leg of the wearer with the exoskeleton.

19. The method of claim 17, wherein, in the balance training mode, the collecting of data includes collecting data on the balance state of the exoskeleton and wearer while the wearer performs one or more of the following movements: standing on one leg; marching in place; shifting weight from leg to leg; shifting weight between legs and crutches; sidestepping; or backstepping.

20. The method of claim 17, wherein, the trajectory cycle mode, the trajectory cycle is modified by changing one or more of the following parameters: step height; step length; step time; or step spacing.

* * * * *